United States Patent
Bloemer et al.

(10) Patent No.: US 9,956,415 B2
(45) Date of Patent: May 1, 2018

(54) EPICARDIAL HEART STIMULATOR

(71) Applicant: BIOTRONIK SE & CO. KG, Berlin (DE)

(72) Inventors: Frank Bloemer, Berlin (DE); Christian Moss, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 0 days. days.

(21) Appl. No.: 14/965,153

(22) Filed: Dec. 10, 2015

(65) Prior Publication Data
US 2016/0193467 A1 Jul. 7, 2016

Related U.S. Application Data

(60) Provisional application No. 62/100,099, filed on Jan. 6, 2015.

(51) Int. Cl.
*A61N 1/36* (2006.01)
*A61N 1/368* (2006.01)
(Continued)

(52) U.S. Cl.
CPC .......... *A61N 1/368* (2013.01); *A61N 1/0587* (2013.01); *A61N 1/3756* (2013.01);
(Continued)

(58) Field of Classification Search
CPC .. A61N 1/368; A61N 1/0587; A61N 1/37205; A61N 1/3756; A61N 1/36507;
(Continued)

(56) References Cited

U.S. PATENT DOCUMENTS

2006/0069322 A1* 3/2006 Zhang ............... A61B 5/04011
600/512
2006/0085041 A1 4/2006 Hastings et al.
(Continued)

FOREIGN PATENT DOCUMENTS

WO 2013152259 10/2013

OTHER PUBLICATIONS

European Search Report received from EP Application Serial No. 15195554.9 dated May 12, 2016, 9 pages.

*Primary Examiner* — Michael Carey
*Assistant Examiner* — Natasha Patel
(74) *Attorney, Agent, or Firm* — Arc IP Law, PC; Joseph J. Mayo (57) ABSTRACT

Embodiments include an epicardial heart stimulator that includes a housing and electric components arranged in the housing. The electric components include a stimulation unit, a stimulation control unit, and at least one stimulation electrode on the housing. The stimulation electrode is connected to the stimulation unit and to the stimulation control unit. The stimulation unit provides electric energy that corresponds to a stimulation pulse and delivers the stimulation pulse via the stimulation electrode upon a corresponding trigger signal of the stimulation control unit. The epicardial heart stimulator includes a sensing electrode on the housing that senses electric potentials and that is electrically connected to a sensing unit in the housing. The sensing unit is connected to the stimulation control unit. The stimulation control unit, in a corresponding operating mode, controls the delivery of a respective trigger signal in accordance with an output signal of the sensing unit.

12 Claims, 6 Drawing Sheets

(51) Int. Cl.
  *A61N 1/05* (2006.01)
  *A61N 1/375* (2006.01)
  *A61N 1/372* (2006.01)
  *A61B 5/0452* (2006.01)
  *A61N 1/365* (2006.01)

(52) U.S. Cl.
  CPC ........ *A61N 1/37205* (2013.01); *A61B 5/0452* (2013.01); *A61N 1/36507* (2013.01)

(58) Field of Classification Search
  CPC ...... A61N 1/375; A61N 1/059; A61B 5/0452; A61B 5/0031
  See application file for complete search history.

(56) References Cited

U.S. PATENT DOCUMENTS

| | | | |
|---|---|---|---|
| 2007/0088398 A1* | 4/2007 | Jacobson | A61N 1/3708 607/9 |
| 2007/0179540 A1 | 8/2007 | Stegemann et al. | |
| 2009/0088813 A1 | 4/2009 | Brockway et al. | |
| 2009/0275999 A1* | 11/2009 | Burnes | A61N 1/368 607/25 |
| 2013/0079861 A1* | 3/2013 | Reinert | A61N 1/3756 607/126 |
| 2014/0058494 A1* | 2/2014 | Ostroff | A61N 1/0587 607/122 |
| 2015/0088221 A1 | 3/2015 | Barr-Cohen et al. | |

\* cited by examiner

EPICARDIAL HEART STIMULATOR

This application claims the benefit of U.S. Provisional Patent Application 62/100,099 filed on 6 Jan. 2015, the specification of which is hereby incorporated herein by reference.

BACKGROUND OF THE INVENTION

Field of the Invention

Embodiments of the invention generally relate to an epicardial heart stimulator that stimulates a chamber or an antechamber, in particular that stimulates a right or left ventricle of a heart.

Description of the Related Art

Generally, implantable heart stimulators may include cardiac pacemakers. Such heart stimulators are generally connected to electrode lines, which have stimulation or defibrillation electrodes in a chamber of a heart or in the immediate vicinity. Typically, epicardial cardiac pacemakers do not require such electrode lines, but are implanted on the outer side of a heart and stimulate the heart tissue (myocardium) via a stimulation electrode attached to a housing. For example, World Intellectual Property Organization Patent Publication WO 2013152259, to Bar-Cohen et al., entitled "Minimally Invasive Epicardial Pacemaker", appears to disclose an epicardial cardiac pacemaker with a stimulation electrode in the form of a helix.

Generally, a cardiac pacemaker may deliver an electric stimulation pulse to the muscle tissue (myocardium) of a heart chamber via the stimulation electrode so as to thus induce a stimulated contraction of the heart chamber, provided the stimulation pulse has a sufficient intensity and the heart muscle tissue (myocardium) is not in a refractory phase at that precise moment. So as to trigger a stimulated contraction of a heart chamber in this way, typically, stimulation electrodes having a relatively small surface area are usually used, since, in order to trigger a stimulated contraction of a heart chamber, it is sufficient for only a small part of the myocardium of this heart chamber to be stimulated initially. Such a stimulated contraction of a heart chamber may be referred to herein as a stimulated event. A natural contraction of the heart chamber may be referred to herein as a natural action or as an intrinsic event. A contraction for example of the right atrium of a heart may be referred to herein as an atrial event, which for example may be a natural atrial event or, in the case of an atrial cardiac pacemaker, may also be a stimulated atrial event. Generally, (intrinsic) and stimulated left-ventricular and right-ventricular events may be distinguished in a similar manner.

Typically, with regard to the stimulation of a heart chamber, in particular of the right or left ventricle of a heart, it should also be noted that these occur preferably atrium-synchronously so as to reproduce the natural contraction sequence of the heart as effectively as possible. Generally, there is initially a contraction of the right atrium and then, following an atrio-ventricular conduction period, there is a contraction of the right ventricle and, at the same time or shortly after, of the left ventricle. Under certain conditions, typically, the natural contraction of the ventricle is absent in some patients subsequent to a natural contraction of the atrium. In typical dual-chamber pacemakers, the natural contraction of the atrium is therefore detected as an intrinsic atrial event and stimulates the right and/or the left ventricle following a predefined conduction time.

Generally, the detection of such natural (intrinsic) events is achieved by sensing, such as measuring, the electric potentials of the myocardium of the respective heart chamber with the aid of sensing electrodes, which are part of a corresponding electrode line in the case of conventional heart stimulators.

Typically, the detection of intrinsic events in the ventricle makes it possible, for example, to operate a ventricular heart stimulator in demand mode, in which the delivery of ventricular stimulation pulses is then always suppressed when a natural ventricular event is detected within a respective time window. Generally, the detection of intrinsic events in the atrium makes it possible, for example, to deliver ventricular stimulation pulses (provided these are not suppressed) to a ventricular heart stimulator atrium-synchronously, for example after a predefined atrio-ventricular delay period following detection of the respective atrial event.

Typically, the stimulation modes that may be implemented with a heart stimulator may include VVI, VDD, DDD, etc.

Generally, epicardial heart stimulators may be implanted at 4 different positions, depending on which heart chamber or antechamber is to be stimulated, for example left- or right-ventricular or left- or right-atrial.

BRIEF SUMMARY OF THE INVENTION

One or more embodiments of the invention include stimulation modes for epicardial heart stimulators.

At least one embodiment of the invention includes an epicardial heart stimulator that includes a housing and electric components arranged in the housing. In one or more embodiments, the electrical components may include a stimulation unit and a stimulation control unit, and at least one stimulation electrode on the housing. In at least one embodiment, the at least one stimulation electrode is connected to the stimulation unit, and the stimulation unit is connected to the stimulation control unit. In one or more embodiments, the stimulation unit may provide electric energy that corresponds to a stimulation pulse, and may deliver the stimulation pulse via the at least one stimulation electrode upon a corresponding trigger signal of the stimulation control unit. At least one embodiment may include at least one sensing electrode on the housing that senses electric potentials, and a sensing unit in the housing. In one or more embodiments, the at least one sensing electrode is electrically connected to the sensing unit. In at least one embodiment, the sensing unit may be electrically connected to the stimulation control unit, and the stimulation control unit may, in a corresponding operating mode, control the delivery of a respective trigger signal in accordance with an output signal of the sensing unit.

The inventors have found that the sensing of intrinsic signals, for example of an epicardial heart stimulator, is generally local and therefore only the identification of the activity in one chamber may be possible. Typically, since epicardial heart stimulators have only local electrode (poles) attached to the housing thereof, the sensing electrodes are generally also adjacent to the heart chamber or antechamber that is to be stimulated. With an epicardial heart stimulator as such, only sensing in the chamber adjacent to the epicardial heart pacemaker is generally possible, and therefore a cardiac pacemaker as such may also provide single-chamber operating modes, such as AAI or VVI.

One or more embodiments of the invention include the identification of the activity in a distant chamber, such as a chamber other than the chamber adjacent to the epicardial cardiac pacemaker as discussed above. At least one embodiment may include a ventricular epicardial cardiac pacemaker, wherein the ventricular epicardial cardiac pacemaker may sense atrial events and may deliver an atrium-synchronous stimulation, for example in VDD mode, with an individual epicardially placed ventricular cardiac stimulator, and without the need for a second implanted device.

One or more embodiments of the invention may include one or more sensing electrodes in the housing of the epicardial cardiac stimulator, wherein the one or more sensing electrodes may adopt a spatially maximal distance such that the far-field signals from remote chambers may be perceived and used for the timing.

By way of at least one embodiment, the sensing unit may be connected to a sensing electrode of the at least one sensing electrode, and to the stimulation electrode or a second sensing electrode of the at least one sensing electrode. In one or more embodiments, the stimulation control unit may evaluate the output signal of the sensing unit in terms of or based on one or more signal features that indicate a contraction of a remote antechamber and/or a heart chamber. In at least one embodiment, the output signal of the sensing unit may be, or may include, a far-field electrocardiogram, such that the sensing unit may be, or may include, a far-field sensing unit.

At least one embodiment may include a plurality of sensing electrodes that sense electric potentials. In one or more embodiments, the sensing unit may include a switch, to which one or two of the plurality of sensing electrodes are electrically connected, in a switchable manner, to other components of the sensing unit that may record an electrocardiogram.

One or more embodiments may include an indifferent electrode pole on the housing in the immediate vicinity of the at least one stimulation electrode and forms, together with the at least one stimulation electrode, a stimulation electrode pair. In at least one embodiment, the indifferent electrode pole may be formed by, or may include, a ring electrode, which at least partially surrounds the at least one stimulation electrode. In one or more embodiments, the indifferent electrode pole may be formed by, or may include, another electrode, having a greater surface area compared with the stimulation electrode, in the vicinity of the stimulation electrode.

In at least one embodiment, the stimulation electrode may be, or may include, a pin electrode or helix electrode. In one or more embodiments, a helix electrode may allow a fastening of the epicardial heart stimulator by screwing the helix electrode into the myocardium in a manner similar to a corkscrew.

In at least one embodiment, the epicardial heart stimulator may be, may be formed as or may include, a ventricular cardiac pacemaker, such that the stimulator may be operated atrium-synchronously, at least in a VDD operating mode.

In one or more embodiments, the epicardial heart stimulator may be, or may include, a demand pacemaker, wherein the demand pacemaker may detect intrinsic events of a respective chamber to be stimulated and may suppress a delivery of a stimulation pulse if an intrinsic activity of the respective heart chamber is detected within a corresponding time window.

In at least one embodiment of the invention, the epicardial heart stimulator may be, or may include, a rate-adaptive pacemaker, which may adapt a stimulation rate to a hemodynamic need of a respective patient.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
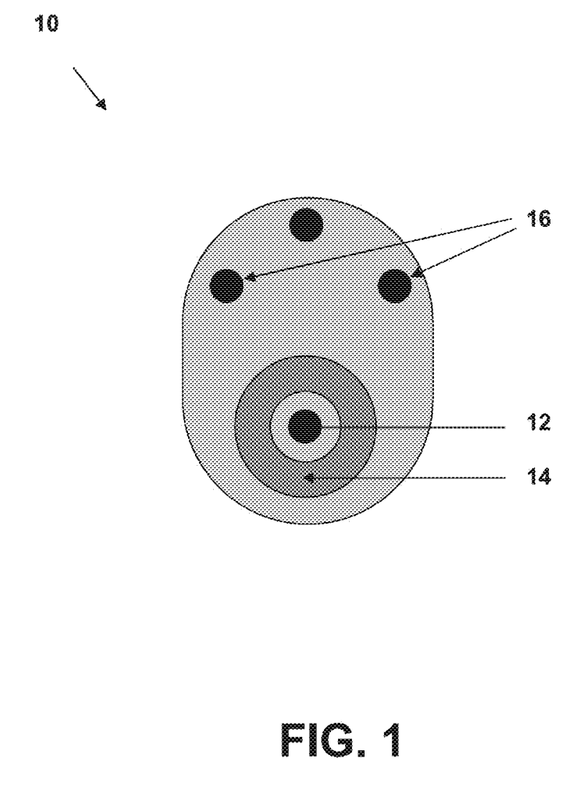
FIG. 1 shows a side view of an epicardial cardiac pacemaker facing the heart after implantation.

FIG. 1 shows a side view of an epicardial cardiac pacemaker 10 facing the heart after implantation, according to one or more embodiments of the invention. As shown in FIG. 1, at least one embodiment may include a pin or helix electrode 12 as a different stimulation electrode pole on the side of the epicardial cardiac pacemaker 10. One or more embodiments may include a ring electrode 14 as indifferent electrode pole around the pin or helix electrode 12. In at least one embodiment, the pin or helix electrode 12 and the ring electrode 14 may stimulate the heart chamber or antechamber arranged adjacently to the epicardial cardiac pacemaker 10 after implantation. As shown in FIG. 1, one or more embodiments may include sensing electrodes 16 at a greatest possible distance from the pin or helix electrode 12.

Figure 2:
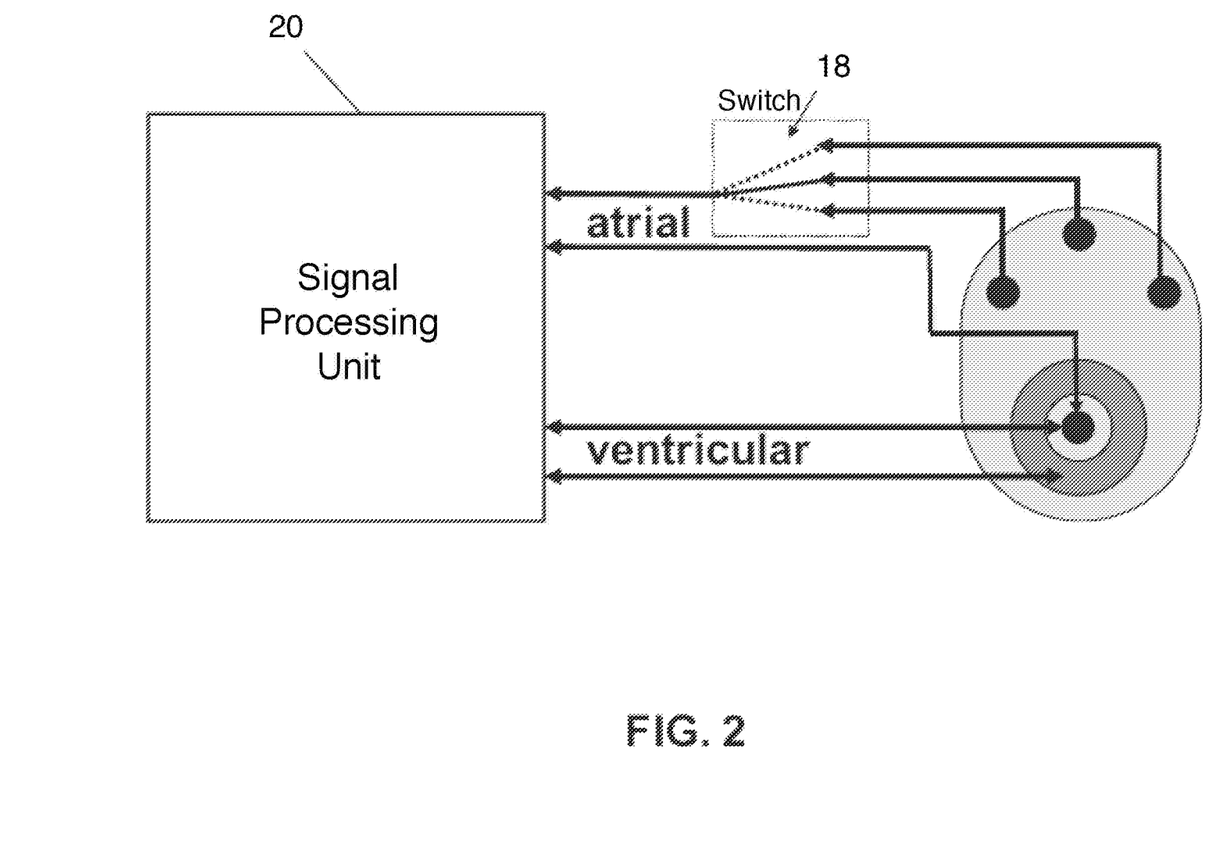
FIG. 2 shows a diagram of the wiring of the electrodes of the epicardial cardiac pacemaker of FIG. 1 with a pacemaker logic and signal processing unit.

FIG. 2 shows a diagram of the wiring of the electrodes of the epicardial cardiac pacemaker of FIG. 1 with a pacemaker logic and signal processing unit, according to one or more embodiments of the invention. As shown in FIG. 2, in at least one embodiment, the sensing electrodes 16, such as three sensing electrodes, are connected via a programmable switch 18 to a pacemaker logic and signal processing unit 20. In one or more embodiments, the pin or helix electrode 12 and the ring electrode 14 may be connected to the pacemaker logic and signal processing unit 20.

In at least one embodiment, with the epicardial heart stimulator 10 as a ventricular cardiac pacemaker, the pin or helix electrode 12 may form, or may include, the ventricular stimulation electrode, and the ring electrode 14 may form, or may include, the corresponding counter-electrode.

Figure 6:
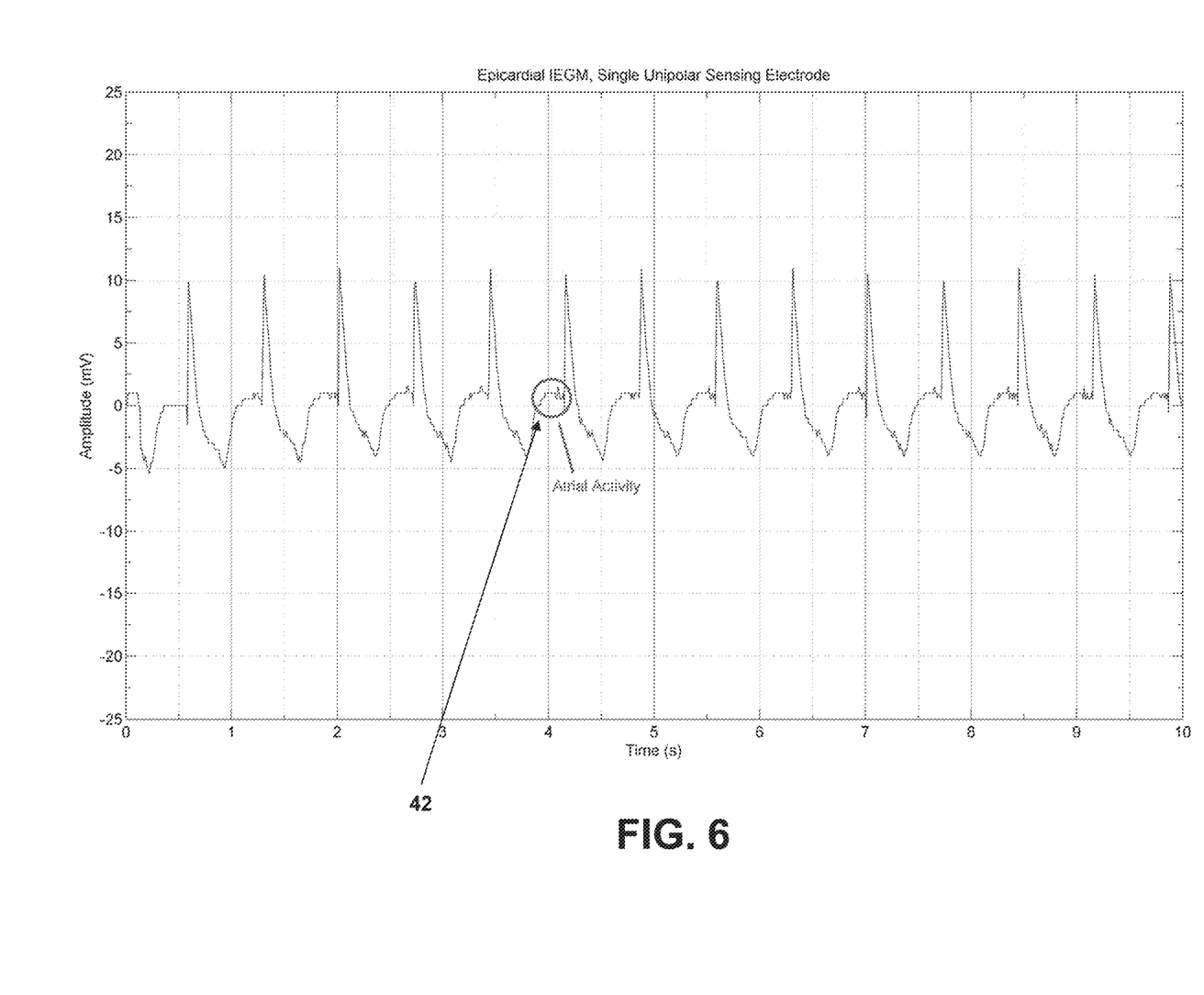
FIG. 6 shows extracardial signals recorded by an epicardial cardiac pacemaker; according to one or more embodiments of the invention.

In one or more embodiments, the pin or helix electrode 12 together with one of the sensing electrodes 16 may detect electric potential profiles representing a far-field electrocardiogram, for example as shown in FIG. 6. In at least one embodiment, the programmable switch 18 allows the sensing electrode 16 that delivers the signal together with the pin or helix electrode 12 to connect to a corresponding far-field sensing unit of the pacemaker logic and signal processing unit 20.

Figure 3:
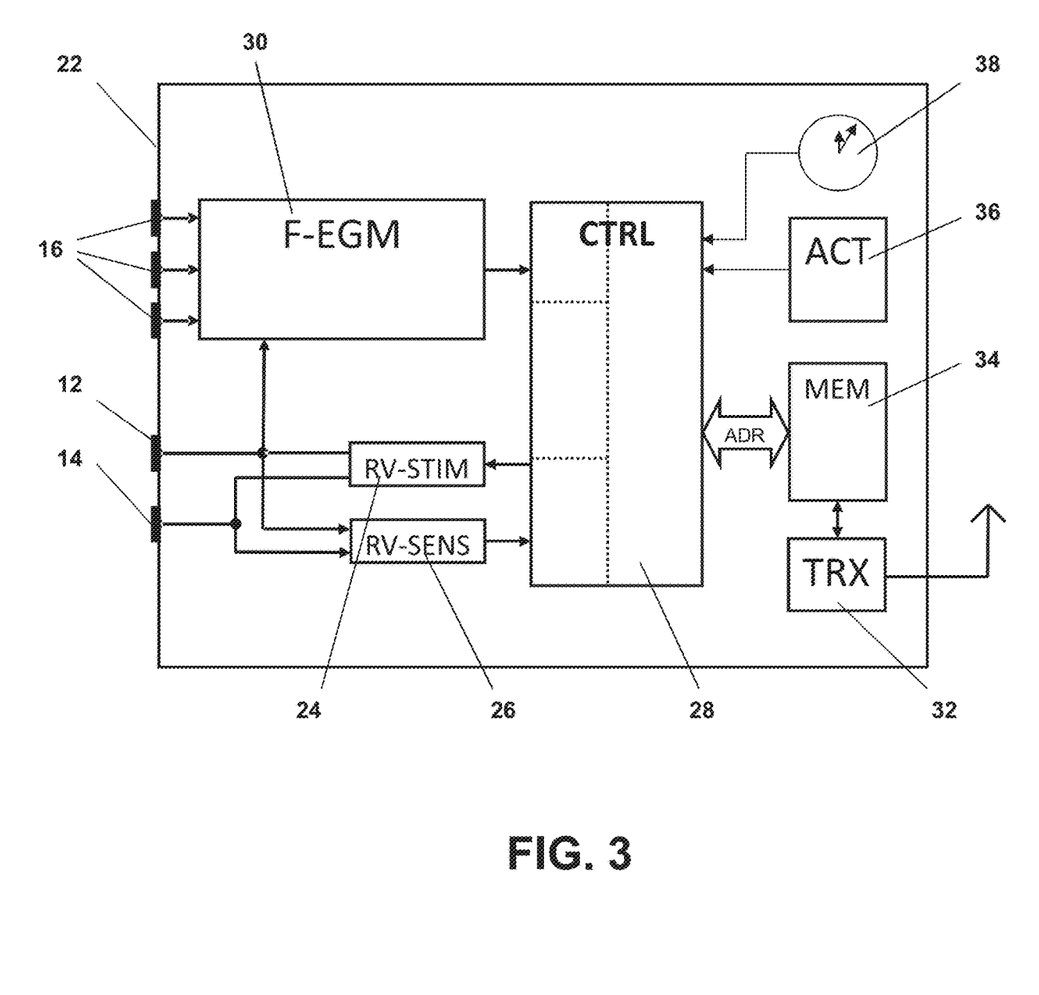
FIG. 3 shows a schematic block diagram of the main components of the pacemaker logic and signal processing unit.

FIG. 3 shows a schematic block diagram of the main components of the pacemaker logic and signal processing unit 20, according to one or more embodiments of the invention. As shown in FIG. 3, in at least one embodiment, the pacemaker logic and signal processing unit 20 is located in a housing 22 of the epicardial heart stimulator 10, wherein the stimulation electrode 12, the ring electrode 14 and the sensing electrodes 16 are located on a surface of the housing.

In one or more embodiments, the stimulation electrode 12 and the ring electrode 14 are each connected to both a stimulation unit 24 and to a sensing unit 26. In at least one embodiment, the epicardial heart stimulator may be, or may include, a right-ventricular cardiac pacemaker, wherein the stimulation unit 24 is a right-ventricular stimulation unit and the sensing unit 26 is a right-ventricular sensing unit. In one or more embodiments, the stimulation unit 24 may provide the energy that corresponds to a stimulation pulse and may deliver the stimulation pulse upon a trigger signal to adjacent tissue via the stimulation electrode 12. In at least one embodiment, the stimulation unit 24 may be connected to a stimulation control unit 28, which generates a corresponding trigger signal. In one or more embodiments, the sensing unit 26 may detect local heart events via the stimulation electrode 12 and the ring electrode 14, such as heart events that are associated with the chamber located adjacently to the epicardial heart stimulator 10. In one or more embodiments with a ventricular cardiac pacemaker, the sensing unit 26 may detect right-ventricular events and may deliver a corresponding output signal to the stimulation control unit 28 in the event of detection of a respective ventricular event. As such, in at least one embodiment, the stimulation unit 28 may trigger stimulation pulses only as required, specifically when the sensing unit 26 has not detected an intrinsic ventricular event.

By way of at least one embodiment, the sensing electrodes 16, such as the three sensing electrodes, may be connected to a far-field sensing unit 30, which is connected via a further input to the stimulation electrode 12. In one or more embodiments, the far-field sensing unit 30 may evaluate the potential difference between one of the sensing electrodes 16, such as one of the three sensing electrodes, and the stimulation electrode, for example of a far-field electrocardiogram. In at least one embodiment, the far-field sensing unit 30 may include a programmable switch 18, as shown in FIG. 2, wherein the programmable switch 18 may deliver and/or use one of the (three) sensing electrodes 16 to sense. According to one or more embodiments, instead of three sensing electrodes 16, a single sensing electrode or four or more sensing electrodes may be included. In at least one embodiment with a single sensing electrode 16, the programmable switch 18 may be omitted. In one or more embodiments, the far-field sensing unit 30 may deliver an output signal to the stimulation control unit 28, for example as shown in FIG. 6, wherein the output signal includes signal features that signal or indicate, for example, atrial activity. With the aid of the far-field sensing unit 30, in at least one embodiment, the stimulation control unit 28 may detect, for example, atrial events when the epicardial heart stimulator 10 is, or includes, a ventricular cardiac pacemaker, for example adjacently to the right ventricle.

For example, one or more embodiments may include an atrium-synchronous, need-dependent stimulation of the right ventricle, for example via the epicardial heart stimulator shown in FIG. 3.

As shown in FIG. 3, by way of at least one embodiment, the stimulation control unit 28 may be connected to a memory unit 30, which for example may store control signals or may store signal profiles recorded by the epicardial heart stimulator 10. In order to reprogram the epicardial heart stimulator 10 or transmit recorded signal profiles to an external device to evaluate the signal profiles, in one or more embodiments, the epicardial cardiac pacemaker 10 may include a telemetry unit 34, which is connected to the memory 32. In order to adjust stimulation rates suitable for the hemodynamic need of a respective patient, in at least one embodiment, the stimulation control unit 28 may be connected to an activity sensor 36, such that the epicardial heart stimulator 10 may be or may include a rate-adaptive cardiac pacemaker. In one or more embodiments, the activity sensor 36 may be or may include a sensor, which delivers an output signal dependent on the hemodynamic need of a patient. In at least one embodiment, the stimulation control unit 28 may be connected to a timer unit 38.

Figure 4:
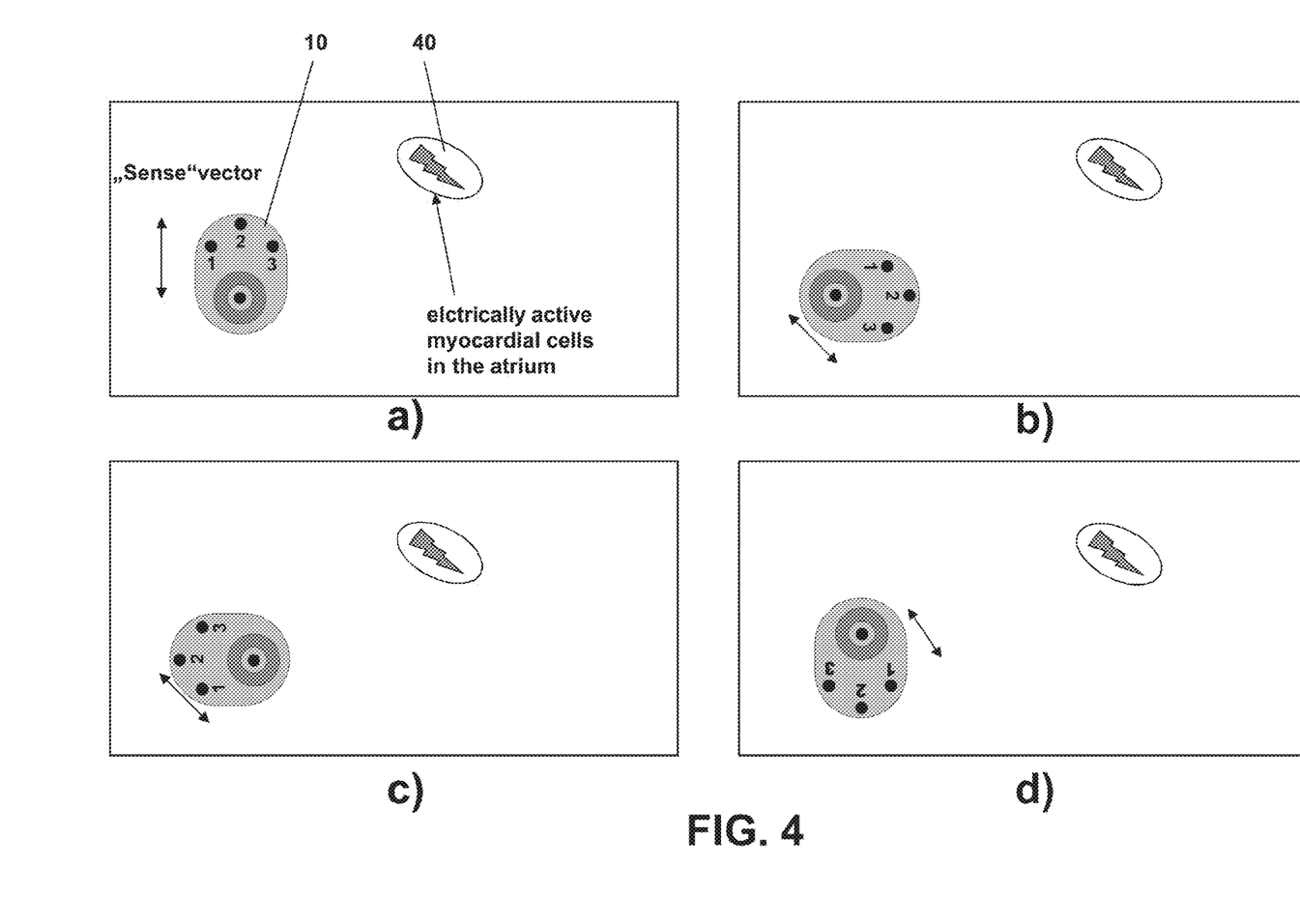
FIG. 4 shows different possible orientations of the epicardial cardiac pacemaker of FIG. 1 following implantation.

FIG. 4 shows different possible orientations of the epicardial cardiac pacemaker of FIG. 1 following implantation, according to one or more embodiments of the invention. By way of at least one embodiment, FIG. 4 shows, via orientations a), b), c) and d), the three stimulation electrodes 16 of the epicardial stimulator 10 that may fix a sensing vector with one of the sensing electrodes 16 and one of the stimulation electrodes 12. As such, via the sensing vector fixed with one of the sensing electrodes 16 and one of the stimulation electrodes 12, one or more embodiments may detect a meaningful far-field electrocardiogram signal via the different orientations of the heart stimulator 10, shown at orientations a), b), c) and d), with respect to electrically active heart muscle cells 40, such as electrically active myocardial cells in the atrium.

Figure 5:
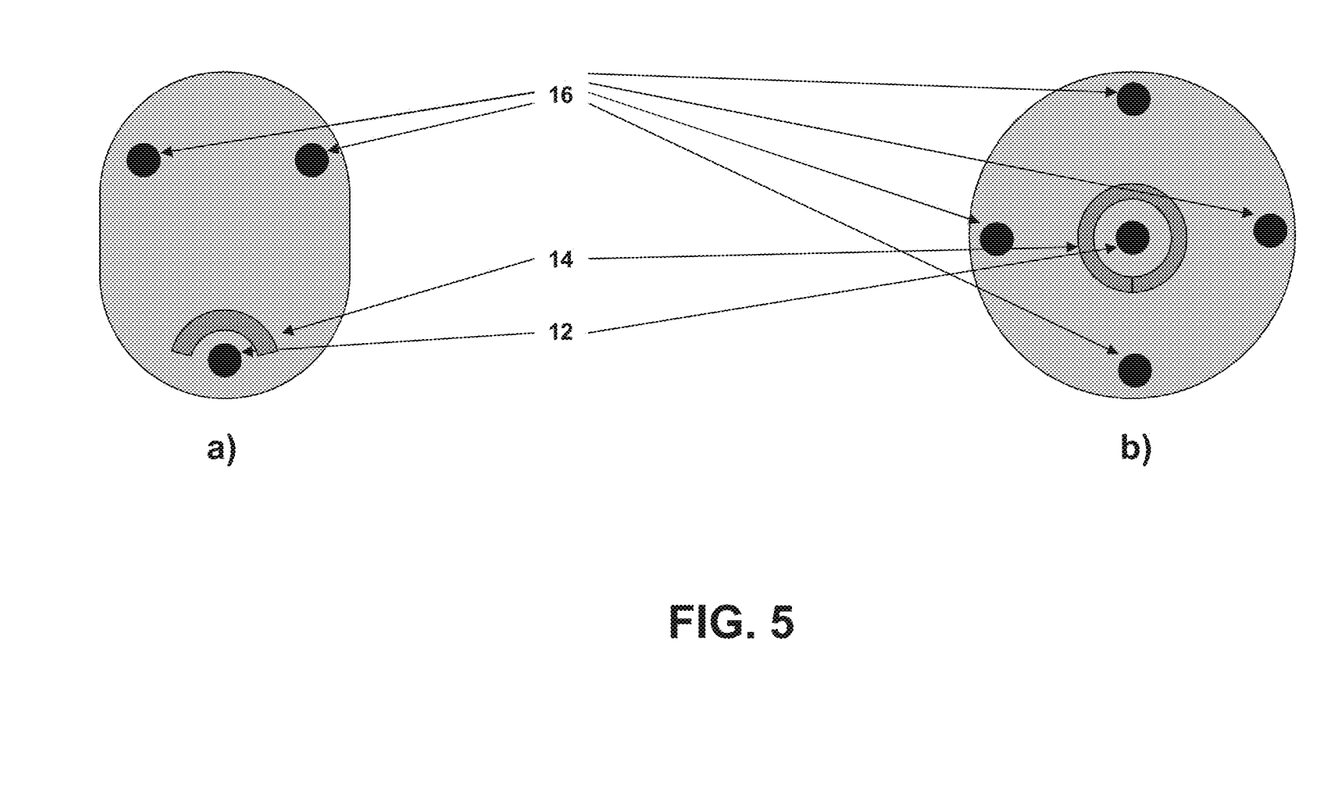
FIG. 5 shows two alternative variants of an epicardial cardiac pacemaker.

FIG. 5 shows, by way of at least one embodiment, alternative variants of electrode numbers and arrangements. As shown in variant a) of FIG. 5, in one or more embodiments, the indifferent electrode pole may not have to be formed by or include a ring electrode, but for example may be formed by, or may include, a half-ring or a different, slightly greater surface area. As shown in variant a) of FIG. 5, instead of three sensing electrodes 16, one or more embodiments may include only two sensing electrodes.

At least one embodiments of the invention, as shown in variant b) of FIG. 5, may include a central arrangement of the different electrode pole (pin or helix electrode 12), with indifferent ring electrode 14 arranged therearound. In at least one embodiment, four sensing electrodes 16 may be arranged at the greatest distance possible from the different stimulation electrode pole 12. By way of one or more embodiments with a configuration as shown in variant b) of FIG. 4, a greater number of different sensing vectors may be formed. In at least one embodiment, sensing may be performed via two of the four sensing electrodes. As such, in one or more embodiments, the far-field sensing unit may not be connected to a sensing electrode and the different stimulation electrode pole, but may be connected to two sensing electrodes.

FIG. 6 shows extracardial signals recorded by an epicardial cardiac pacemaker, according to one or more embodiments of the invention. As shown in FIG. 6, by way of at least one embodiment, an extracardial electrocardiogram may be recorded using an epicardial heart stimulator 10. In one or more embodiments, a signal portion 42 representing an atrial event may be marked.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS 10 cardiac pacemaker
12 pin or helix electrode
14 ring electrode
16 sensing electrode
18 switch
20 signal processing unit
22 housing
24 stimulation unit
26 sensing unit
28 stimulation control unit
30 far-field sensing unit
32 memory
34 telemetry unit
36 activity sensor
38 timer unit
40 electrically active myocardial cells
42 atrial event in the far-field electrocardiogram

What is claimed is:

1. An epicardial heart stimulator comprising:
a housing;
at least three stimulation electrodes on the housing;
at least one sensing electrode on the housing configured to sense electric potentials;
a sensing unit within the housing; and,
electric components within the housing, wherein the electric components comprise
  a stimulation unit connected to the at least three stimulation electrodes, and,
  a stimulation control unit connected to the stimulation unit,
  wherein the stimulation unit is configured to
    provide electric energy that corresponds to a stimulation pulse, and
    deliver the stimulation pulse via the at least three stimulation electrodes upon detection of a corresponding trigger signal of the stimulation control unit;
wherein the at least one sensing electrode is electrically connected to the sensing unit,
wherein the sensing unit is connected to the stimulation control unit,
wherein the stimulation control unit, in a corresponding operating mode, controls a delivery of a respective trigger signal in accordance with an output signal of the sensing unit,
wherein a sensing vector is fixed with one of the at least three stimulation electrodes and one of the at least one sensing electrode, and
wherein a far-field electrocardiogram signal is detected with the sensing vector via different orientations of the epicardial heart stimulator.

2. The epicardial heart stimulator according to claim 1, wherein the sensing unit is connected to
  the at least one sensing electrode, and
  the at least three stimulation electrodes or a second sensing electrode of the at least one sensing electrode, and
wherein the stimulation control unit is configured to evaluate the output signal of the sensing unit based on signal features that indicate a contraction of one or more of a distant antechamber and a heart chamber.

3. The epicardial heart stimulator according to claim 1,
wherein the at least one sensing electrode comprises a plurality of sensing electrodes on the housing configured to sense electric potentials,
wherein the sensing unit comprises a switch, wherein one or two of the plurality of sensing electrodes are electrically connected switchably to other components of the sensing unit via said switch, and
wherein the sensing unit is configured to record an electrocardiogram.

4. The epicardial heart stimulator according to claim 1, further comprising an indifferent electrode pole on the housing, wherein the indifferent electrode pole is located in an immediate vicinity of the at least three stimulation electrodes.

5. The epicardial heart stimulator according to claim 4, wherein the indifferent electrode pole comprises a ring electrode, wherein the ring electrode at least partially surrounds one of the at least three stimulation electrodes.

6. The epicardial heart stimulator according to claim 1, wherein one of the at least three stimulation electrodes is a pin or helix electrode.

7. The epicardial heart stimulator according to claim 1, wherein the epicardial heart stimulator is a ventricular cardiac pacemaker configured to operate atrium-synchronously at least in a VDD operating mode.

8. The epicardial heart stimulator according to claim 1, wherein the epicardial heart stimulator is a demand pacemaker.

9. The epicardial heart stimulator according to claim 1, wherein the epicardial heart stimulator is a rate-adaptive pacemaker.

10. The epicardial heart stimulator according to claim 4, wherein the indifferent electrode pole comprises a ring electrode with a greater surface area than one of the at least three stimulation electrodes, wherein the ring electrode fully encircles one of the at least three stimulation electrodes.

11. The epicardial heart stimulator according to claim 4, wherein the indifferent electrode pole comprises a greater surface area than one of the at least three stimulation electrodes, such that the indifferent electrode at least partially encircles one of the at least three stimulation electrodes.

12. The epicardial heart stimulator according to claim 1, wherein the epicardial heart stimulator is a ventricular cardiac pacemaker configured to operate atrium-synchronously as an individual epicardially placed ventricular cardiac pacemaker without a second implanted device.

* * * * *